(12) United States Patent
Vaidya et al.

(10) Patent No.: US 12,424,334 B1
(45) Date of Patent: Sep. 23, 2025

(54) APPARATUS AND METHOD FOR GENERATING PSEUDO-ELECTROGRAM (EGM) DATA FROM ELECTROCARDIOGRAM (ECG) DATA

(71) Applicant: Anumana, Inc., Cambridge, MA (US)

(72) Inventors: Suthirth Vaidya, Bengaluru (IN); Rakesh Barve, Bengaluru (IN); Animesh Agarwal, San Mateo, CA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/786,969

(22) Filed: Jul. 29, 2024

(51) Int. Cl.
*G16H 50/70* (2018.01)
*A61B 5/346* (2021.01)
*G06N 20/00* (2019.01)

(52) U.S. Cl.
CPC ............. *G16H 50/70* (2018.01); *G06N 20/00* (2019.01)

(58) Field of Classification Search
CPC ........ G16H 50/50; G16H 50/30; G16H 50/70; G16H 50/20; G16H 10/60; A61B 5/0006; A61B 5/349; A61B 5/346
See application file for complete search history.

(56) References Cited

U.S. PATENT DOCUMENTS

| 8,359,089 | B2 | 1/2013 | Makdissi |
| 2008/0243200 | A1 | 10/2008 | Scinicariello et al. |
| 2020/0345261 | A1* | 11/2020 | Haeusser ............... A61B 5/361 |
| 2020/0352466 | A1 | 11/2020 | Chakravarthy et al. |
| 2024/0065637 | A1* | 2/2024 | Goil ....................... G16H 10/60 |

FOREIGN PATENT DOCUMENTS

WO   WO-2024091557 A1 *  5/2024  .............. A61B 5/29

OTHER PUBLICATIONS

Rodrigo, M., Pagano, B., et al. (2021, June). Intra-cardiac signatures of atrial arrhythmias identified by machine learning and traditional features. In International Conference on Functional Imaging and Modeling of the Heart (pp. 671-678). Cham: Springer International Publishing. (Year: 2021).*
A Banta et al; A Novel Convolutional Neural Network for Reconstructing Surface Electrocardiograms from Intracardiac Electrograms and Vice Versa; Artif Intell Med. Aug. 2021; 118: 102135.Published online Jul. 16, 2021.

* cited by examiner

*Primary Examiner* — Jason B Dunham
*Assistant Examiner* — Constantine Siozopoulos
(74) *Attorney, Agent, or Firm* — Caldwell Intellectual Property Law

(57) ABSTRACT

Apparatus and method for generating pseudo-EGM data from ECG data are disclosed. The apparatus includes at least a processor and a memory communicatively connected to the at least a processor, wherein the memory contains instructions configuring the at least a processor to generate EGM model training data, wherein generating the EGM model training data includes receiving the EGM model training data, wherein the EGM model training data includes exemplary ECG data correlated to exemplary EGM data and time synchronizing the exemplary ECG data and the exemplary EGM data, train an EGM machine-learning model using the EGM model training data, receive subject data, wherein the subject data includes subject ECG data and generate subject EGM data as a function of the subject ECG data using the trained EGM machine-learning model.

20 Claims, 8 Drawing Sheets

APPARATUS AND METHOD FOR GENERATING PSEUDO-ELECTROGRAM (EGM) DATA FROM ELECTROCARDIOGRAM (ECG) DATA

FIELD OF THE INVENTION

The present invention generally relates to the field of machine-learning. In particular, the present invention is directed to an apparatus and method for generating pseudo-electrogram (EGM) data from electrocardiogram (ECG) data.

BACKGROUND

Intracardiac electrograms (EGMs) are essential tools in the field of cardiac electrophysiology, providing detailed recordings of the heart's electrical activity from within the cardiac chambers. Unlike surface electrocardiograms (ECGs), which capture the heart's electrical signals from electrodes placed on the skin, EGMs offer a more precise and localized view of the electrical conduction pathways within the heart. However, EGMs require the insertion of catheters into the heart chambers, and this invasive procedure carries risks and patients can experience discomfort or pain, requiring a recovery period.

SUMMARY OF THE DISCLOSURE

In an aspect, an apparatus for generating pseudo-EGM data from ECG data is disclosed. The apparatus includes at least a processor and a memory communicatively connected to the at least a processor, wherein the memory contains instructions configuring the at least a processor to generate EGM model training data, wherein generating the EGM model training data includes receiving the EGM model training data, wherein the EGM model training data includes exemplary ECG data correlated to exemplary EGM data and time synchronizing the exemplary ECG data and the exemplary EGM data, train an EGM machine-learning model using the EGM model training data, receive subject data, wherein the subject data includes subject ECG data and generate subject EGM data as a function of the subject ECG data using the trained EGM machine-learning model.

In another aspect, a method for generating pseudo-EGM data from ECG data is disclosed. The method includes generating, using at least a processor, EGM model training data, wherein generating the EGM model training data includes receiving the EGM model training data, wherein the EGM model training data includes exemplary ECG data correlated to exemplary EGM data and time synchronizing the exemplary ECG data and the exemplary EGM data, training, using the at least a processor, an EGM machine-learning model using the EGM model training data, receiving, using the at least a processor, subject data, wherein the subject data includes subject ECG data and generating, using the at least a processor, subject EGM data as a function of the subject ECG data using the trained EGM machine-learning model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for generating pseudo-EGM data from ECG data are disclosed. The apparatus includes at least a processor and a memory communicatively connected to the at least a processor, wherein the memory contains instructions configuring the at least a processor to generate EGM model training data, wherein generating the EGM model training data includes receiving the EGM model training data, wherein the EGM model training data includes exemplary ECG data correlated to exemplary EGM data and time synchronizing the exemplary ECG data and the exemplary EGM data, train an EGM machine-learning model using the EGM model training data, receive subject data, wherein the subject data includes subject ECG data and generate subject EGM data as a function of the subject ECG data using the trained EGM machine-learning model.

Aspects of the present disclosure allow for the avoidance of performing an EGM test on a patient. This is beneficial because EGM test procedures are significantly more invasive than ECG test procedures—thus, they would be beneficial to avoid. Exemplary embodiments illustrating aspects of the present disclosure are described below in the context of several specific examples.

Figure 1:
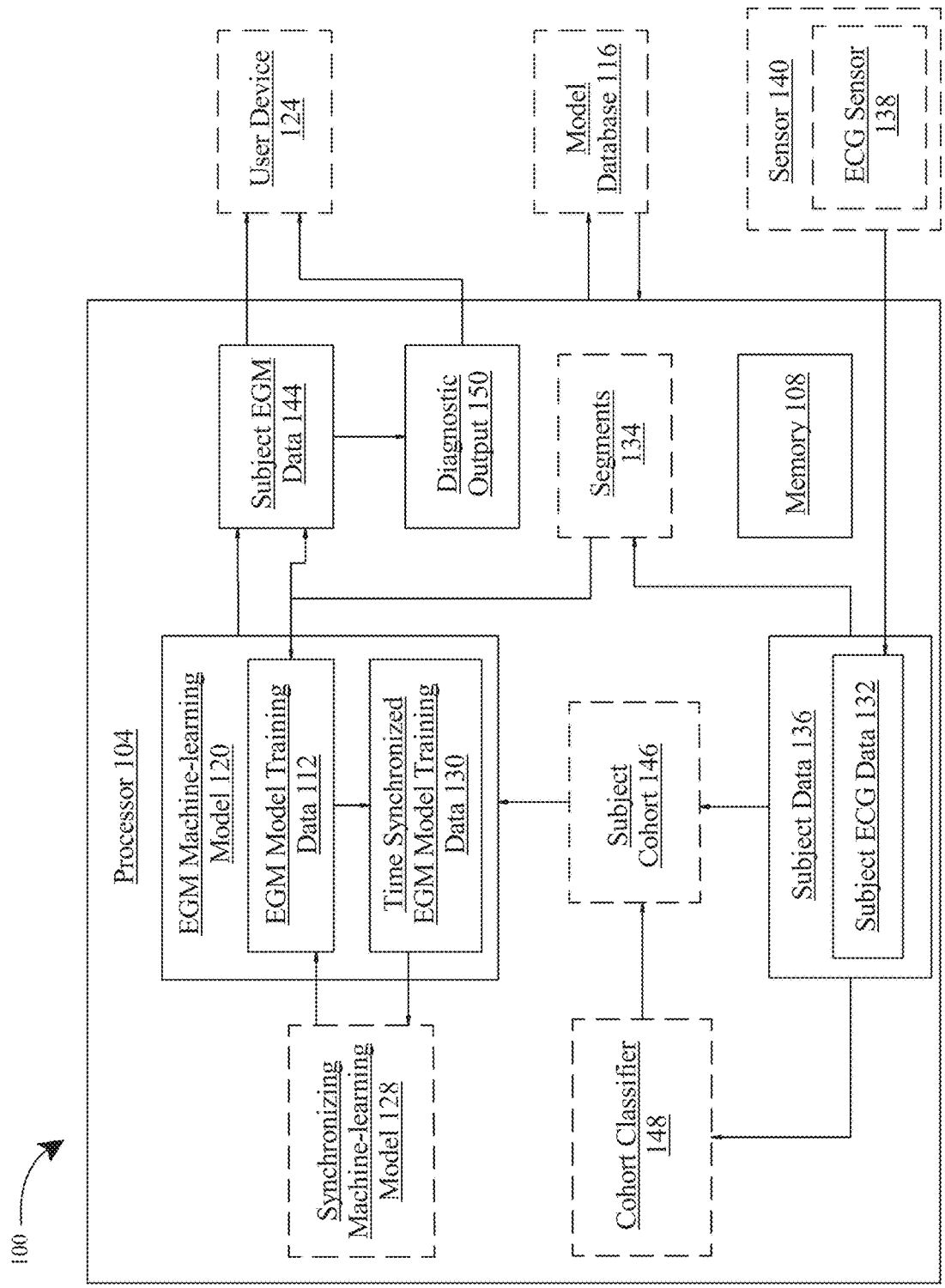
FIG. 1 illustrates a block diagram of an exemplary apparatus for generating pseudo-EGM data from ECG data.

Referring now to FIG. 1, an exemplary embodiment of an apparatus 100 for generating pseudo-EGM data from ECG data is illustrated. Apparatus 100 includes at least a processor 104. Processor 104 may include, without limitation, any processor described in this disclosure. Processor 104 may be included in a computing device. Processor 104 may include any computing device as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory 108 communicatively connected to processor 104. For the purposes of this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 108 contains instructions configuring processor 104 to generate EGM model training data 112. For the purposes of this disclosure, "EGM model training data" is a set of data used to train an electrogram (EGM) machine learning model. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from model database 116, such as any model database 116 described in this disclosure, or be provided by a user. In other embodiments, a machine-learning module may obtain a training set by querying a communicatively connected model database 116 that includes past inputs and outputs. Training data may include inputs from various types of databases, resources, and/or user inputs and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements. Machine learning module may be used to generate a machine learning model and/or any other machine learning model using training data. Machine learning model may be trained by correlated inputs and outputs of training data. Training data may be data sets that have already been converted from raw data whether manually, by machine, or any other method. Training data may be stored in model database 116. Training data may also be retrieved from model database 116. In some embodiments, EGM model training data 112 may be received from one or more users, model database 116, external computing devices, and/or previous iterations of processing. As a non-limiting example, EGM model training data 112 may include instructions from a user, who may be an expert user, a past user in embodiments disclosed herein, or the like, which may be stored in memory and/or stored in model database 116, where the instructions may include labeling of training examples. In some embodiments, processor 104 may retrieve EGM model training data 112 from a database of a health organization, hospital, and the like or electronic health record (EHR) system. For the purposes of this disclosure, an "electronic health record" is the systematized collection of patient and population electronically stored health information in a digital format. In some embodiments, EGM model training data 112 may be updated iteratively using a feedback loop. As a non-limiting example, processor 104 may update EGM model training data 112 iteratively through a feedback loop as a function of user cohort, ECG data, EGM data, input and output of EGM machine-learning model 120, or the like.

With continued reference to FIG. 1, processor 104 is configured to generate EGM model training data 112. EGM model training data 112 includes correlations between exemplary electrocardiogram (ECG) data and exemplary electrogram (EGM) data.

With continued reference to FIG. 1, for the purposes of this disclosure, "electrocardiogram data" is information related to the electrical activity of the heart over a period of time. In one or more embodiments, ECG data may include a matrix having a plurality of electrocardiogram signals and/or associated time variables. A "matrix" for the purposes of this disclosure is an array of numbers or characters arranged in rows or columns which are used to represent an object or properties of the object. For example, and without limitation, a matrix may be used to describe linear equations, differential equations, in a two-dimensional format. In another non limiting example, a matrix may be used to create graphs based on data points, generate statistical models and the like. In one or more embodiments, matrix may include a plurality of electrocardiogram signals associated with a plurality of time variables. As used in the current disclosure, a "electrocardiogram signal" is a signal representative of electrical activity of heart. The ECG signal may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves may provide information about the duration and regularity of various phases of the cardiac cycle. The ECG signal may help diagnose various heart conditions, such as arrhythmias, myocardial infarction (heart attack), conduction abnormalities, and electrolyte imbalances. In one or more embodiments, ECG signals may be received by one or more electrodes connected to the skin of an individual. In one or more embodiments, ECG signals may represent depolarization and repolarization occurring in the heart. In one or more embodiments, ECG signals may be captured periodically. For example, and without limitation, every second, every millisecond and the like.

With continued reference to FIG. 1, in one or more embodiments, each ECG signal may contain an associated time variable. "Time variable" for the purposes of this disclosure is information indicating the time at which a particular ECG signal or EGM signal was received. For example, and without limitation, time variable may include, 5 ms, 10 ms, 15 ms, and the like. In one or more embodiments, each ECG signal may contain a time variable. In one or more embodiments, time variable may increase in given increments, such as for example, in increments of 5 ms, wherein a first time variable may include 5 ms and a second time variable may include 10 ms. In one or more embodiments, a combination of a plurality of ECG signals and correlated time variable may be used to generate a graph illustrating the heart functions of an individual. In one or more embodiments, matrix may include a plurality of ECG signals and correlated time variable during a given time frame such as, for example, over the span of a second, a minute, an hour, and the like. In one or more embodiments, ECG signals may be captured as voltages, such as millivolts or microvolts.

With continued reference to FIG. 1, for the purposes of this disclosure, "electrogram data" refers to recordings of the electrical activity of the heart obtained through invasive procedures. In some embodiments, electrogram data may include recordings obtained by inserting specialized catheters with electrodes directly into the heart chambers or onto specific cardiac structures. In some embodiments, EGM data may include a matrix having a plurality of EGM signals and/or associated time variables. For example, and without limitation, time variable may include, 5 ms, 10 ms, 15 ms, and the like. In one or more embodiments, each EGM signal may contain a time variable. In some embodiments, EGM data may be consistent with ECG data while EGM data may provide a more detailed and precise assessment of the heart's electrical activity compared to surface ECG (e.g., ECG data). In some embodiments, EGM data may include continuous x, y, z coordinates. In a non-limiting example, when EGM data is recorded using catheters or electrodes with known spatial positions, each data point in EGM data may be associated with specific x, y, z coordinates that represent the location within the heart where the electrical signal was measured. In some embodiments, ECG data and EGM data may be collected at the same time from a same patient and processor 104 may generate EGM model training data using the ECG data and EGM data that are simultaneously collected from the same patient.

With continued reference to FIG. 1, in some embodiments, apparatus 100 may include a model database 116. As used in this disclosure, "model database" is a data store configured to store data associated with ECG data and EGM data. As a non-limiting example, model database 116 may store EGM model training data 112, inputs and outputs of EGM machine-learning model 120, and the like. In one or more embodiments, model database 116 may include inputted or calculated information and datum related to ECG data and EGM data. In some embodiments, a datum history may be stored in model database 116. As a non-limiting example, the datum history may include real-time and/or previous inputted data related to ECG data and EGM data. As a non-limiting example, model database 116 may include instructions from a user, who may be an expert user, a past user in embodiments disclosed herein, or the like, where the instructions may include examples of the data related to ECG data and EGM data.

With continued reference to FIG. 1, in some embodiments, processor 104 may be communicatively connected with model database 116. For example, and without limitation, in some cases, model database 116 may be local to processor 104. In another example, and without limitation, model database 116 may be remote to processor 104 and communicative with processor 104 by way of one or more networks. The network may include, but is not limited to, a cloud network, a mesh network, and the like. By way of example, a "cloud-based" system can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connect directly, dynamically, and non-hierarchically to as many other computing devices as possible. A "network topology" as used in this disclosure is an arrangement of elements of a communication network. The network may use an immutable sequential listing to securely store model database 116. An "immutable sequential listing," as used in this disclosure, is a data structure that places data entries in a fixed sequential arrangement, such as a temporal sequence of entries and/or blocks thereof, where the sequential arrangement, once established, cannot be altered or reordered. An immutable sequential listing may be, include and/or implement an immutable ledger, where data entries that have been posted to the immutable sequential listing cannot be altered.

With continued reference to FIG. 1, in some embodiments, model database 116 may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described in this disclosure. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, in some embodiments, processor 104 may receive ECG data and EGM data from user device 124. For the purposes of this disclosure, a "user device" is any device a user can use to input data into apparatus 100. As a non-limiting example, user device 124 may include a laptop, desktop, tablet, mobile phone, smart phone, smart watch, kiosk, smart headset, or things of the like. For the purposes of this disclosure, a "user" is any person, individual, organization or entity that is using or has used an apparatus. As a non-limiting example, user may include a physician, clinician, nurses, doctors, medical professionals, hospitals, medical organization, and the like. In some embodiments, user device 124 may include an interface configured to receive inputs from user. In some embodiments, user may manually input any data into apparatus 100 using user device 124. In some embodiments, user may have a capability to process, store or transmit any information independently.

With continued reference to FIG. 1, processor 104 may receive ECG data and EGM data using an application programming interface (API). As used in the current disclosure, an "application programming interface" is a software interface for two or more computer programs to communicate with each other. As a non-limiting example, API may include EHR APIs, telemedicine APIs, and the like. An application programming interface may be a type of software interface, offering a service to other pieces of software. In contrast to a user interface, which connects a computer to a person, an application programming interface may connect computers or pieces of software to each other. An API may not be intended to be used directly by a person (e.g., the end user) other than a computer programmer who is incorporating it into the software. An API may be made up of different parts which act as tools or services that are available to the programmer. A program or a programmer that uses one of these parts is said to call that portion of the API. The calls that make up the API are also known as subroutines, methods, requests, or endpoints. An API specification may define these calls, meaning that it explains how to use or implement them. One purpose of API may be to hide the internal details of how a system works, exposing only those parts a programmer will find useful and keeping them consistent even if the internal details later change. An API may be custom-built for a particular pair of systems, or it may be a shared standard allowing interoperability among many systems. The term API may be often used to refer to web APIs, which allow communication between computers that are joined by the internet. API may be configured to query for web applications in order to retrieve ECG data and EGM data to another web application, database (e.g., model database 116), medical center patient portal, and the like. An API may be further configured to filter through web applications according to a filter criterion. In this disclosure, "filter criteria" are conditions the web applications must fulfill in order to qualify for API. Web applications may be filtered based on these filter criteria. Filter criteria may include, without limitation, types of medical facilities, location of the medical facility, and the like.

With continued reference to FIG. 1, in some embodiments, processor 104 may time synchronize ECG data and EGM data. For the purposes of this disclosure, "time synchronization" refers to a process of aligning data streams or signals from different sources or devices so that they accurately reflect the same temporal sequence of events. When data are synchronized in time, it may indicate that the data are aligned to the same time reference or time points. As a non-limiting example, time stamps or time variables of ECG data and EGM data may be matched by time. In some embodiments, processor 104 may time synchronize ECG data and EGM data using a synchronizing machine-learning model 128. In some embodiments, processor 104 may be configured to generate synchronization training data. In a non-limiting example, synchronization training data may include exemplary ECG data, EGM data correlated to time synchronized ECG data and time synchronized EGM data and synchronizing machine-learning model 128 trained with synchronization training data may time synchronized ECG and time synchronized EGM data that is used to generate time synchronized EGM model training data 130. In some embodiments, synchronization training data may be stored in model database 116. In some embodiments, synchronization training data may be received from one or more users, model database 116, external computing devices, and/or previous iterations of processing. As a non-limiting example, synchronization training data may include instructions from a user, who may be an expert user, a past user in embodiments disclosed herein, or the like, which may be stored in memory and/or stored in model database 116, where the instructions may include labeling of training examples. In some embodiments, synchronization training data may be updated iteratively on a feedback loop. As a non-limiting example, processor 104 may update synchronization training data iteratively through a feedback loop as a function of ECG data, EGM data, EGM model training data 112, or the like. In some embodiments, processor 104 may be configured to generate synchronizing machine-learning model. In a non-limiting example, generating first position machine-learning model may include training, retraining, or fine-tuning synchronizing machine-learning model using synchronization training data or updated synchronization training data.

With continued reference to FIG. 1, in some embodiments, processor 104 may time synchronize ECG data and EGM data by determining a first disturbance in each signal. A "first disturbance" refers to a distinct, identifiable event in a cardiac cycle that appears in both ECG and EGM signals. In some embodiments, R-wave peak in the QRS complex may be used as this first disturbance. The QRS complex represents the rapid depolarization of the right and left ventricles. By identifying this feature as the first disturbance, processor 104 may establish a reliable temporal anchor point for time synchronization. The exact moments of these peaks may be then marked, extracting their time stamps (e.g., time variables). Processor 104 then calculate the time offset between the two signals by subtracting the time stamp of the first disturbance in the ECG signal from the time stamp of the first disturbance in the EGM signal. Lastly, the ECG and EGM signals (e.g., ECG data and EGM data) may be aligned by adjusting the time axis of one of the signals by the calculated offset.

With continued reference to FIG. 1, in some embodiments, processor 104 may time synchronize EGM data and ECG data using dynamic time warping (DTW) based on a similarity matrix. Dynamic time warping may include algorithms for measuring similarity between two sequences, which may vary in time or speed. For instance, similarities in time variables of ECG data and EGM data may be detected, even if in data is slower than the other and if in another data is faster than the other, or even if there were accelerations and deceleration. DTW can been applied to video, audio, signals, and graphics—any data that can be turned into a linear representation can be analyzed with DTW. In some cases, DTW may allow processor 104 to find an optimal match between two given sequences (e.g., time series [time variables of ECG data and EGM data]) with certain restrictions. That is, in some cases, sequences can be "warped" non-linearly to match each other.

With continued reference to FIG. 1, memory 108 contains instructions configuring processor 104 to train an EGM machine-learning model 120 using EGM model training data 112. For the purposes of this disclosure, an "EGM machine-learning model" is a computational artifact created to recognize patterns, make decisions, and predict outcomes related to electrogram based on input data. In some embodiments, processor 104 may be configured to generate EGM machine-learning model 120. In a non-limiting example, generating EGM machine-learning model 120 may include training, iteratively training, retraining, or fine-tuning EGM machine-learning model 120 using EGM model training data 112 or updated EGM model training data 112. In some embodiments, processor 104 may be configured to generate subject ECG data 132 using EGM machine-learning model 120 (i.e. trained or updated EGM machine-learning model 120) as described further in detail below.

With continued reference to FIG. 1, memory 108 contains instructions configuring processor 104 to receive subject data 136. For the purposes of this disclosure, "subject data" is information related to a subject. As a non-limiting example, subject data may include subject's demographic, medical history, billing and insurance information, communication history, and the like. For the purposes of this disclosure, a "subject" is an individual who receives medical care, treatment, or consultation from a user. As a non-limiting example, subject may include a patient. For example, and without limitation, subject may include a patient undergoing electrocardiogram using ECG sensor 138. Subject data 136 includes subject ECG data 132. For the purposes of this disclosure, "subject ECG data" is ECG data related to a subject. The subject ECG data 132 may be consistent with ECG data. In some embodiments, user may manually input subject data 136 and subject ECG data 132. In some embodiments, processor 104 may retrieve subject data 136 and subject ECG data 132 from a model database 116.

With continued reference to FIG. 1, in some embodiments, processor 104 may receive subject ECG data 132 from at least a sensor 140. For the purposes of this disclosure, a "sensor" is a device that produces an output signal for the purpose of sensing a physical phenomenon. As a non-limiting example, sensor 140 may include an ECG sensor 138. For the purposes of this disclosure, an "ECG sensor" is a device that detects and records the electrical signals produced by the heart during each heartbeat electrocardiogram. For the purposes of this disclosure, an "electrode" is a conductive material or element that facilitates the transmission and reception of electrical signals associated with ultrasound waves. In a non-limiting example, electrode may detect and record electrical activity; for instance, but not limited to, the heart's electrical signals (e.g., ECG signals). In some embodiments, ECG sensor 138 may generate a lead system and collect electrical signals using the leads. For the purposes of this disclosure, a "lead system" is the specific electrode placements on the body and the corresponding electrical views of the heart's activity they provide. As a non-limiting example, ECG signals may be collected using 1, 3, 6, and/or 12 lead systems. In some embodiments, ECG sensor 138 may include 12 lead ECG. In some embodiments, a single-lead ECG may correspond to one of the leads of a 12-lead ECG. For example, and without limitation, one of the leads of the 12-lead ECG to which the single-lead corresponds may be Lead 1, Lead 2, Lead 3, AvF, AvL, AvR, or V1-V6. As another non-limiting example, sensor 140 may include EEG sensor, pulse oximeter, blood pressure monitor, glucose sensor, temperature sensor, wearable fitness tracker, or the like.

With continued reference to FIG. 1, in some embodiments, processor 104 may receive subject data 136 and/or subject ECG data 132 from a user device 124. As a non-limiting example, user device 124 may include a laptop, desktop, tablet, mobile phone, smart phone, smart watch, kiosk, smart headset, or things of the like. As a non-limiting example, user may include a health care provider, hospital, health organization, or the like. In some embodiments, user device 124 may include an interface configured to receive inputs from user. In some embodiments, user may manually input any data into apparatus 100 using user device 124. In some embodiments, user may have a capability to process, store or transmit any information independently.

With continued reference to FIG. 1, processor 104 may receive subject data 136, subject ECG data 132, ECG data, or EGM data from externally supplied databases. As a non-limiting example, subject ECG data 132 may be retrieved from subject records. For the purposes of this disclosure, a "subject record" is comprehensive documentation contained medical information about an individual, including medical history, diagnoses, treatments, medications, laboratory results, compiled for healthcare purposes. As a non-limiting example, subject record may include electric health records (EHR). In some embodiments, the receipt of subject records may include communicating with a database (e.g., model database 116, and the like) or databases responsible for hosting subject medical record information. In some embodiments, subject records may be included in a virtual private network, or a virtual private cloud locally stored on medical facilities or offsite. In some embodiments, subject records may be received over a communications protocol. For the purposes of this disclosure, "communications protocol" is a set of rules describing how to transmit, exchange or receive data across a network. It should be noted that the protocol used in communicating with a database may be standardized or unstandardized and be text-based, binary, or some other base.

With continued reference to FIG. 1, in some embodiments, at least a processor 104 may receive subject ECG data 132 from a wearable device. A "wearable device," as used in this disclosure, is a device on a subject that collects subject ECG data, where "on the person" indicates that the device is portable and is either worn on the subject, inside the subject, in contact with the subject, or in close proximity to the subject. Subject ECG data 132 may include data generated, collected, and/or transmitted by the wearable device and may include wearables worn by subject such as an accelerometer, pedometer, gyroscope, fitness trackers, force monitors, motion sensors; wearables in contact with subject's skin such as in electrocardiography (ECG), electrooculography (EOG), bioimpedance, blood pressure and heart rate monitoring, oxygenation data, biosensors, eye tracking system; wearables that may be placed inside and/or within a subject, and/or devices that may be adapted to be placed outside of subject. Wearable devices may be any devices capably and useful in acquiring, measuring, and/or transmitting subject ECG data 132—body measurements and calculations related to human characteristics.

With continued reference to FIG. 1, memory 108 contains instructions configuring processor 104 to generate subject EGM data 144. Processor 104 is configured to generate subject EGM data 144 as a function of subject ECG data 132 using EGM machine-learning model 120 trained with EGM model training data 112. For the purposes of this disclosure, "subject EGM data" is EGM data related to a specific subject related to subject ECG data. In some embodiments, subject EGM data 144 may include continuous x, y, z coordinates. In a non-limiting example, having continuous x, y, z coordinates may indicate that the spatial positions of the electrodes can be tracked continuously and the spatial location of electrodes or catheters within the heart's chambers can be predicted or tracked, represented by three-dimensional Cartesian coordinates (x, y, z). In some embodiments, user may manually input subject EGM data 144. In some embodiments, processor 104 may retrieve subject EGM data 144 from model database 116.

With continued reference to FIG. 1, in some embodiments, processor 104 may be configured to synchronize subject ECG data 132 with ECG data of EGM model training data 112 in time. In some embodiments, subject ECG data 132 may include ECG signal and each ECG signal may contain an associated time variable. Processor 104, in a non-limiting example, may synchronize the time variable of subject ECG data 132 and ECG data. In some embodiments, processor 104 may synchronize subject ECG data 132 with ECG data using DTW as described above. In some embodiments, processor 104 may split subject ECG data 132 (e.g., synchronized subject ECG data 132) into a plurality of segments 134. As a non-limiting example, processor 104 may split subject ECG data 132 (e.g., synchronized subject ECG data 132) into a plurality of segments 134 as a function of time variables of the subject ECG data 132. In a non-limiting example, a plurality of segments 134 of subject ECG data 132 may include 5, 10, 15, 20 seconds, or any seconds thereof. For example, and without limitation, processor 104 may split subject ECG data 132 into 10 seconds of a segment. In some embodiments, processor 104 may generate subject EGM data 144 as a function of a plurality of segments 134 of subject ECG data 132. In a non-limiting example, processor 104 may generate subject EGM data 144 using 10 seconds of segment of subject ECG data 132.

With continued reference to FIG. 1, in some embodiments, processor 104 may generate cohort training data. In some embodiments, cohort training data may include correlations between exemplary subject data and exemplary subject cohorts. In some embodiments, processor 104 may train a cohort classifier using cohort training data. In some embodiments, processor 104 may classify subject data 136 into one or more subject cohorts 146 using cohort classifier 148. In some embodiments, subject or subject data may be classified to a subject cohort 146 using a cohort classifier 148. Cohort classifier 148 may be consistent with any classifier discussed in this disclosure. Cohort classifier 148 may be trained on cohort training data, wherein the cohort training data may include subject data 136 correlated to subject cohorts 146. As a non-limiting example, subject cohorts 146 may be related to subject's age, gender, weight, address, medical history, and the like. In some embodiments, a subject or subject data 136 may be classified to a subject cohort and processor 104 may determine subject EGM data 144 based on the subject cohort 146 using a machine-learning module as described in detail with respect to FIG. 4 and the resulting output may be used to update EGM model training data 112. In some embodiments, processor 104 may retrain EGM machine-learning model 120 using the updated EGM model training data 112.

With continued reference to FIG. 1, in some embodiments, processor 104 may generate a diagnostic output 150 as a function of subject EGM data 144. For the purposes of this disclosure, a "diagnostic output" is data related to a diagnosis of a subject. As a non-limiting example, diagnostic output 150 may include name of health condition or disease resulted from analyzing subject EGM data 144. For example, and without limitation, diagnostic output 150 may include atrial fibrillation (AFib), ventricular tachycardia (VT), ventricular fibrillation (VF), arrhythmia, and the like. For example, and without limitation, diagnostic output 150 may include issues that affect peripheral nerves, such as peripheral neuropathy and nerve compression syndromes like carpal tunnel syndrome, issues that affect the nerve roots that exit spinal column, such as pinched nerves, cervical (neck) radiculopathy or sciatica, muscle disorders (myopathies), such as muscular dystrophy, polymyositis and dermatomyositis, conditions that affect the motor neurons in brain or spinal cord, such as amyotrophic lateral sclerosis (ALS) or post-polio syndrome, conditions that affect the connection between nerves and muscles, such as myasthenia gravis. In some embodiments, user may manually input diagnostic output 150. In some embodiments, processor 104 may retrieve diagnostic output 150 from model database 116.

With continued reference to FIG. 1, in some embodiments, processor 104 may be configured to generate diagnosis training data. In a non-limiting example, diagnosis training data may include correlations between exemplary subject EGM data or exemplary EGM data and exemplary diagnosis outputs. In some embodiments, diagnosis training data may be stored in model database 116. In some embodiments, diagnosis training data may be received from one or more users, model database 116, external computing devices, and/or previous iterations of processing. As a non-limiting example, diagnosis training data may include instructions from a user, who may be an expert user, a past user in embodiments disclosed herein, or the like, which may be stored in memory and/or stored in model database 116, where the instructions may include labeling of training examples. In some embodiments, diagnosis training data may be updated iteratively on a feedback loop. As a non-limiting example, processor 104 may update diagnosis training data iteratively through a feedback loop as a function of subject EGM data 144, subject ECG data 132, output of EGM machine-learning model, subject cohorts 146, and the like. In some embodiments, processor 104 may be configured to generate diagnosis machine-learning model. In a non-limiting example, generating diagnosis machine-learning model may include training, retraining, or fine-tuning diagnosis machine-learning model using diagnosis training data or updated diagnosis training data. In some embodiments, processor 104 may be configured to determine diagnostic output 150 using diagnosis machine-learning model (i.e. trained or updated diagnosis machine-learning model). In some embodiments, subject or subject EGM data 144 may be classified to a subject cohort 146 using a cohort classifier 148. Cohort classifier 148 may be consistent with any classifier discussed in this disclosure. Cohort classifier 148 may be trained on cohort training data, wherein the cohort training data may include subject or subject EGM data 144 correlated to subject cohorts 146. In some embodiments, subject or subject EGM data 144 may be classified to a subject cohort 146 and processor 104 may determine diagnostic output 150 based on the subject cohort using a machine-learning module as described in detail with respect to FIG. 4 and the resulting output may be used to update diagnosis training data. In some embodiments, generating training data and training machine-learning models may be simultaneous.

With continued reference to FIG. 1, processor 104 may be configured to transmit subject EGM data 144 to a user device 124 to display subject EGM data 144, diagnostic output 150, subject ECG data 132, and the like to a user. In some embodiments, at least a processor 104 may be further configured to generate a user interface displaying subject EGM data 144, diagnostic output 150, subject ECG data 132, and the like. For the purposes of this disclosure, a "user interface" is a means by which a user and a computer system interact; for example through the use of input devices and software. A user interface may include a graphical user interface (GUI), command line interface (CLI), menu-driven user interface, touch user interface, voice user interface (VUI), form-based user interface, any combination thereof and the like. In some embodiments, user interface may operate on and/or be communicatively connected to a decentralized platform, metaverse, and/or a decentralized exchange platform associated with the user. For example, a user may interact with user interface in virtual reality. In some embodiments, a user may interact with the use interface using a computing device distinct from and communicatively connected to at least a processor 104. For example, a smart phone, smart, tablet, or laptop operated by a user. In an embodiment, user interface may include a graphical user interface. A "graphical user interface," as used herein, is a graphical form of user interface that allows users to interact with electronic devices. In some embodiments, GUI may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access.

Figure 2:
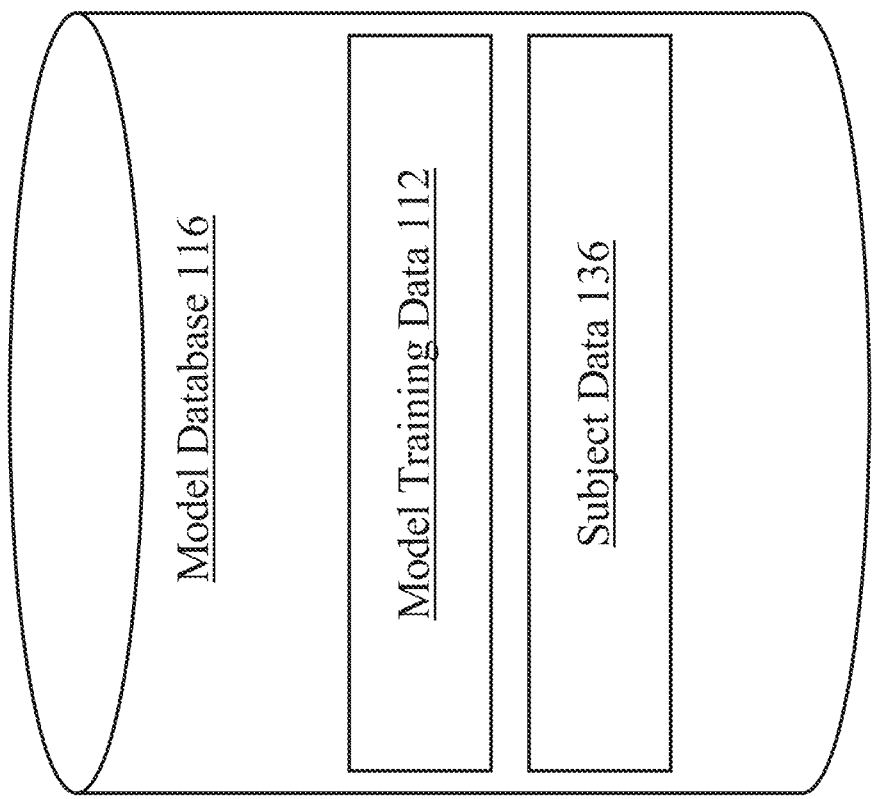
FIG. 2 illustrates a block diagram of an exemplary model database.

Referring now to FIG. 2, a block diagram of an exemplary model database 116 is illustrated. In some embodiments, model database 116 may store data related to EGM machine-learning model 120. As a non-limiting example, model database 116 may store EGM model training data 112, input and output of EGM machine-learning model 120 including subject ECG data 132, subject EGM data 144, and the like. In some embodiments, model database 116 may store cohort training data, subject cohorts 146, input and output of cohort classifier 148, input and output of other machine-learning models described in this disclosure, and the like.

Figure 3:
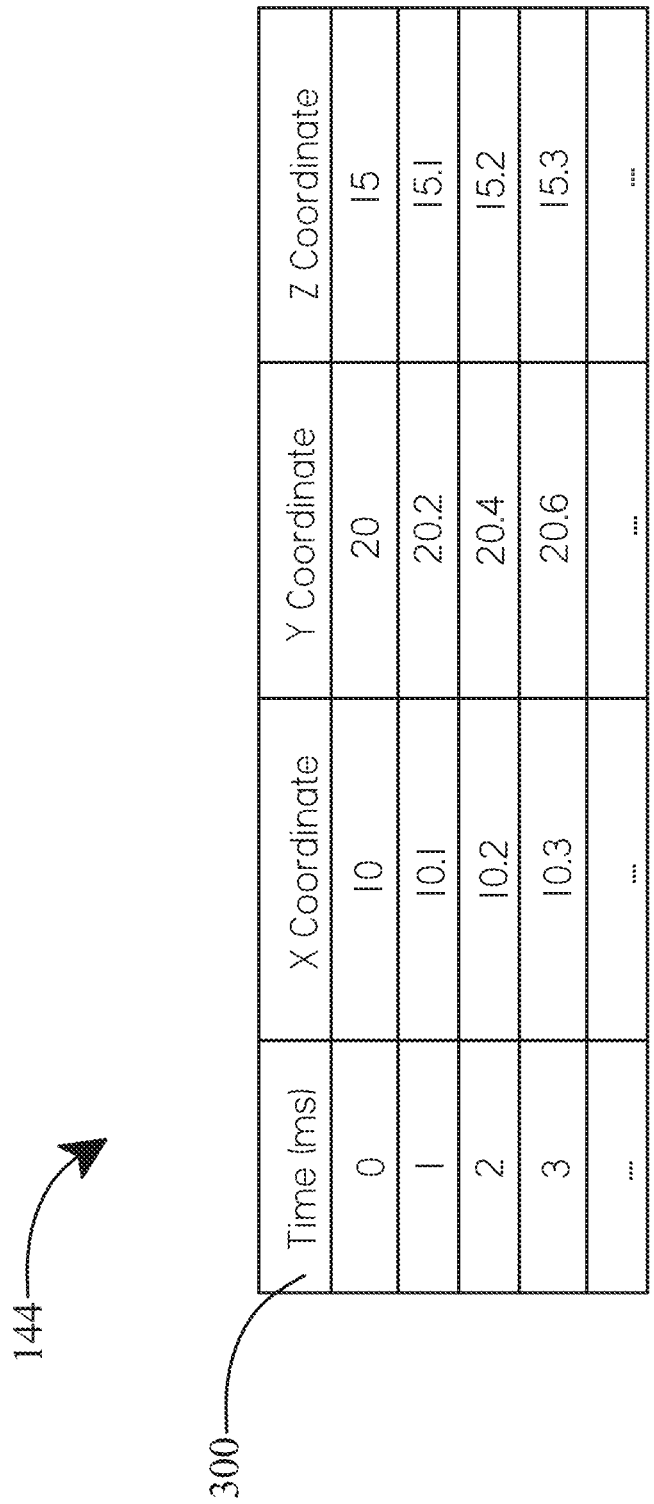
FIG. 3 illustrates a configuration of an exemplary subject EGM data.

Referring now to FIG. 3, an exemplary configuration of exemplary subject EGM data 144 is illustrated. In some embodiments, subject EGM data 144 may include continuous x, y, z coordinates. In FIG. 3, subject EGM data 144 is illustrated in tabular form. However, the tabular form of subject EGM data 144 is mere example and subject EGM data 144 may include various other forms. As a non-limiting example, subject EGM data 144 may include text, graph, and the like. In some embodiments, subject EGM data 144 may include time variables 300. In a non-limiting example, as subject ECG data 132 is segmented into a plurality of segments 134 and one segment of subject ECG data 132 is used to generate subject EGM data 144, subject EGM data 144 may include the same time variables 300 as a segment of subject ECG data 132. For example, and without limitation, if subject ECG data 132 include 10 seconds of a segment, then subject EGM data 144 may include 10 seconds of time variables 300.

Figure 4:
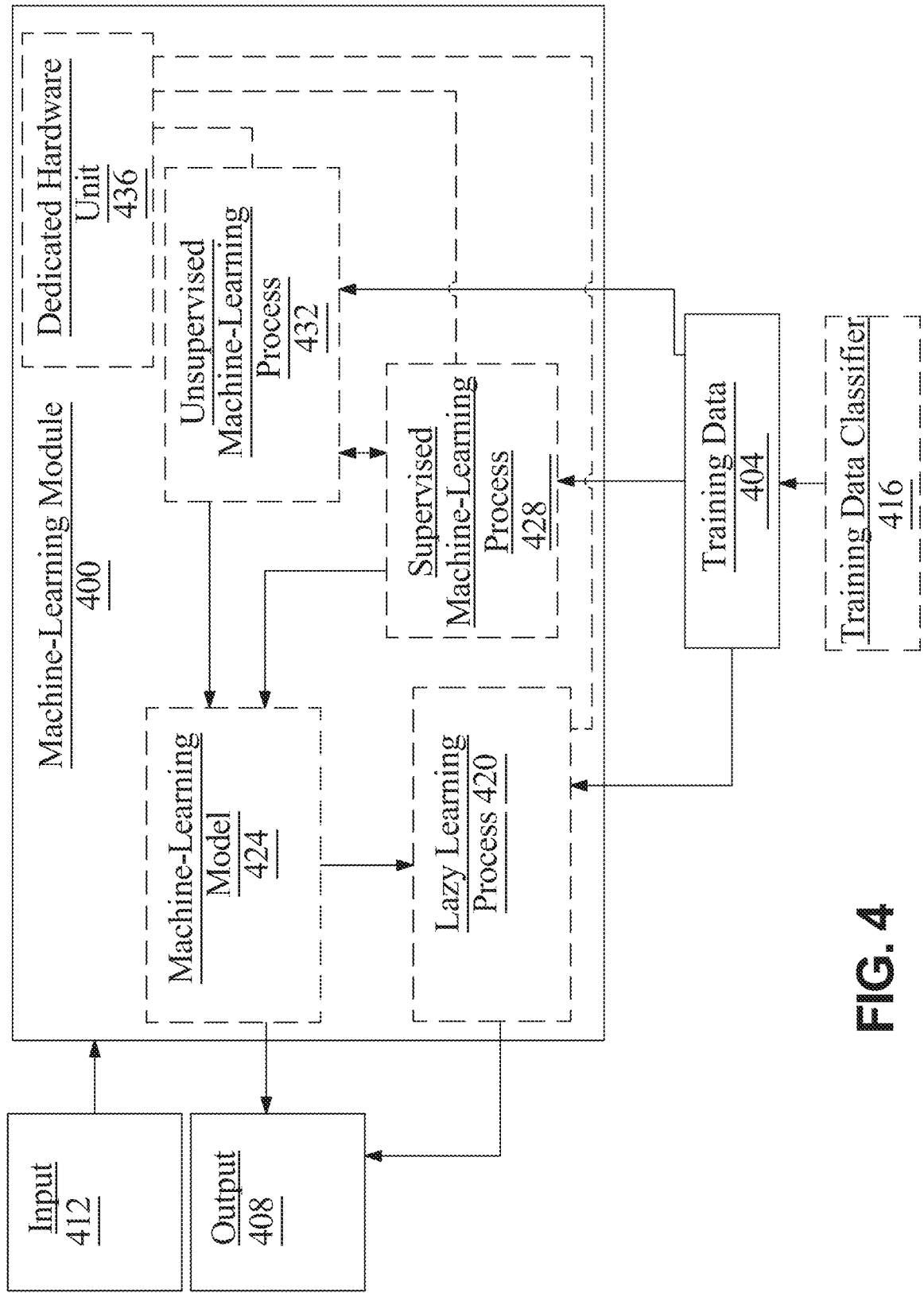
FIG. 4 illustrates a block diagram of an exemplary machine-learning module.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process,"

as used in this disclosure, is a process that automatedly uses training data 404 to generate an algorithm instantiated in hardware or software logic, data structures, and/or functions that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example, input data may include ECG data, EGM data, subject ECG data, subject cohorts, user cohorts, and the like. As a non-limiting illustrative example, output data may include EGM data, subject cohorts, user cohorts, subject EGM data, and the like.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to subject cohorts, user cohorts, and the like. As a non-limiting example, training data classifier 416 may classify elements of training data to subject cohorts related to a subject's age, gender, medical history, weight, ethnicity, and the like. As another non-limiting example, training data classifier 416 may classify elements of training data to user cohorts related to a user's age, gender, medical experience, and the like.

Still referring to FIG. 4, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(A/B)$ is the probability of hypothesis A given data B also known as posterior probability; $P(B/A)$ is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 4, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 4, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 4]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 4, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 4, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 4, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 4, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 4, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 4, computing device, processor, and/or module may down-sample elements of a training example to a desired lower number of data elements. As a non-limiting example, a high pixel count image may have 256 pixels, however a desired number of pixels may be 128. Processor may downsample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 4, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 4, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max} : X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the 50 percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 4, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include ECG data, EGM data, subject ECG data, subject cohorts, user cohorts, and the like as described above as inputs, EGM data, subject cohorts, user cohorts, subject EGM data, and the like as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

With further reference to FIG. 4, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 4, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 432 may not require a response variable; unsupervised processes 432may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 4, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 4, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 4, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 4, one or more processes or algorithms described above may be performed by at least a dedicated hardware unit 436. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 436 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 436 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 436 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 5:
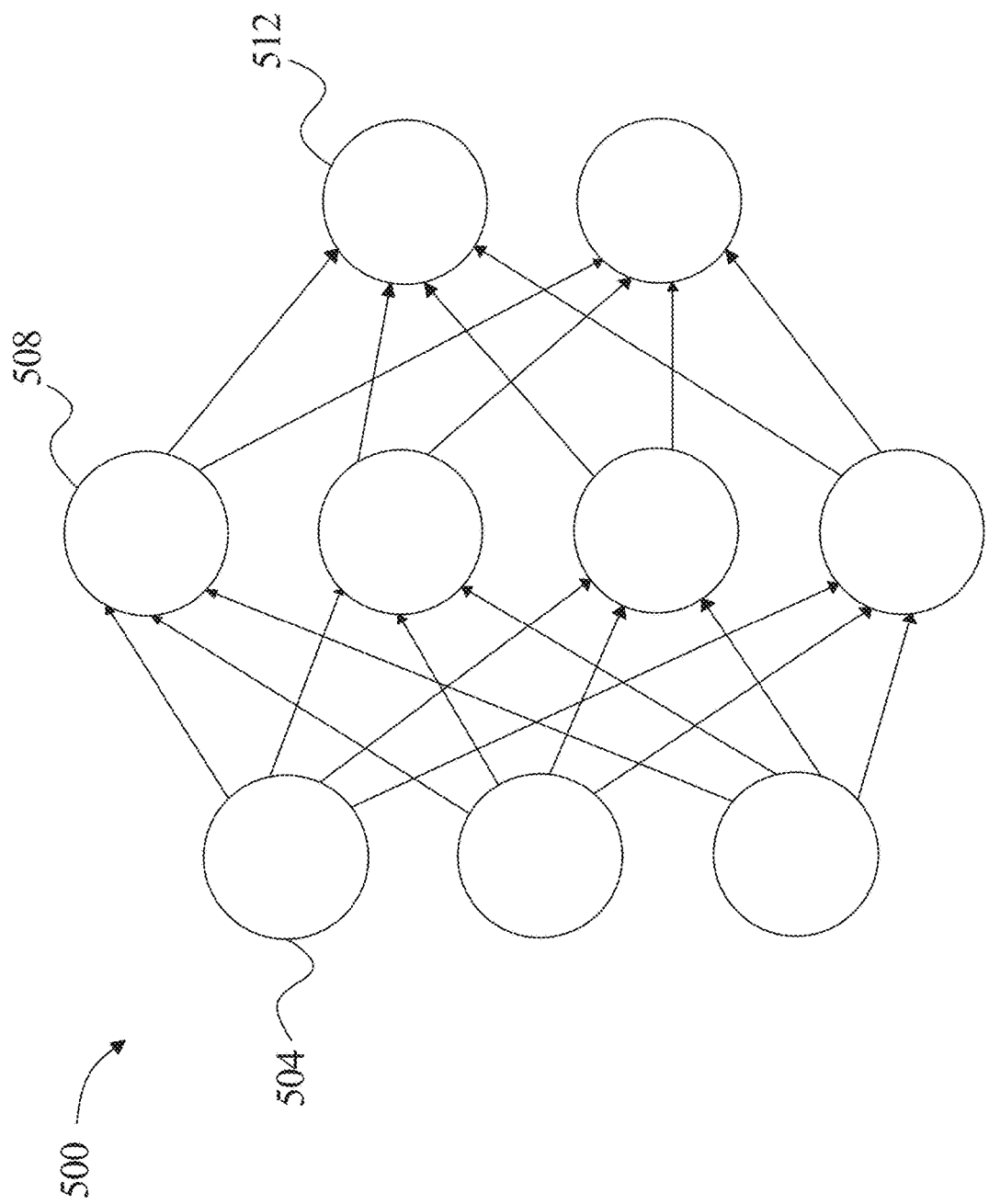
FIG. 5 illustrates a diagram of an exemplary neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 6:
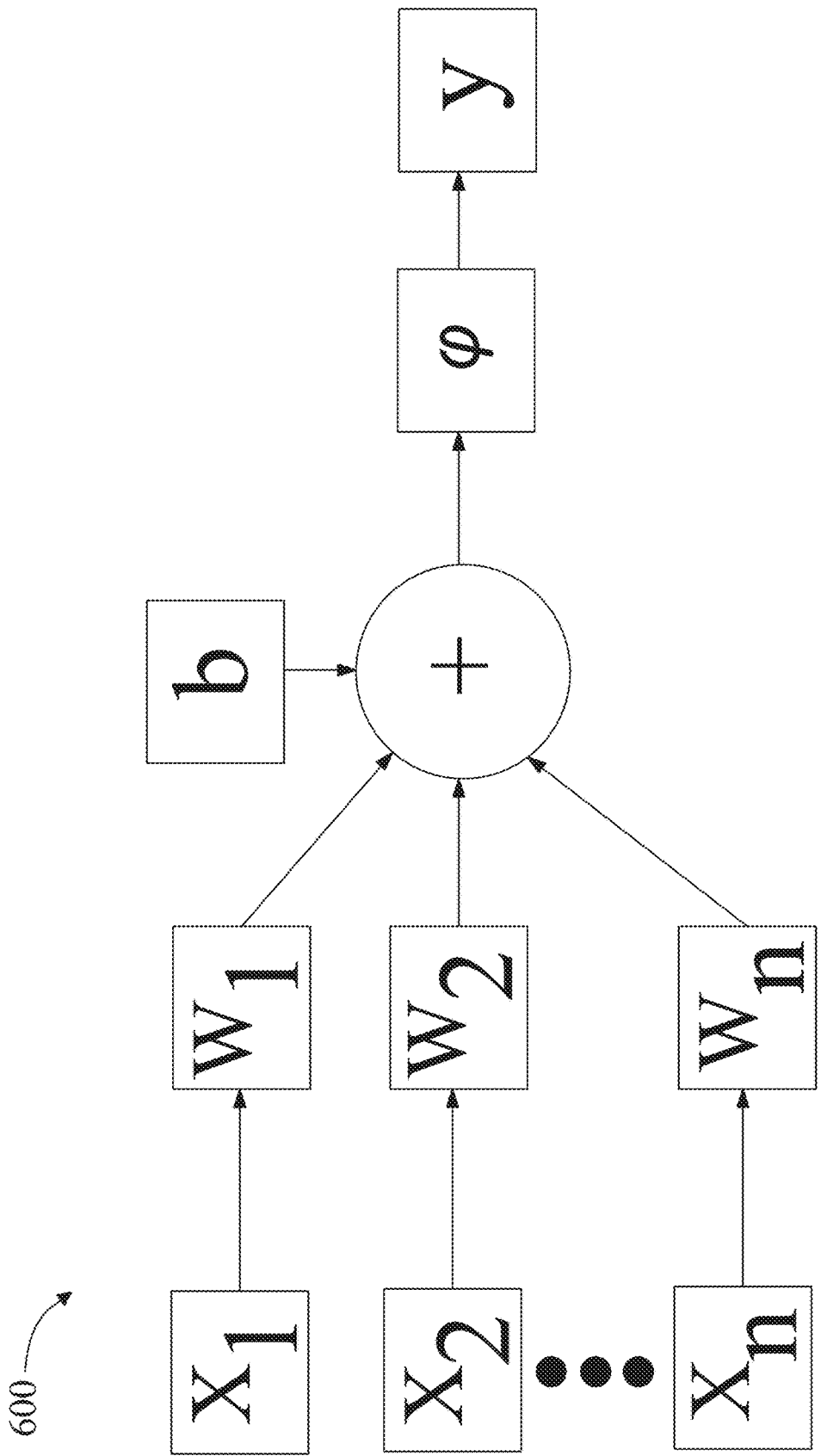
FIG. 6 illustrates a block diagram of an exemplary node in a neural network.

Referring now to FIG. 6, an exemplary embodiment of a node 600 of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1-e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of a (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function p, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_L$ may be determined by training a neural network using training data, which may be performed using any suitable process as described above.

Figure 7:
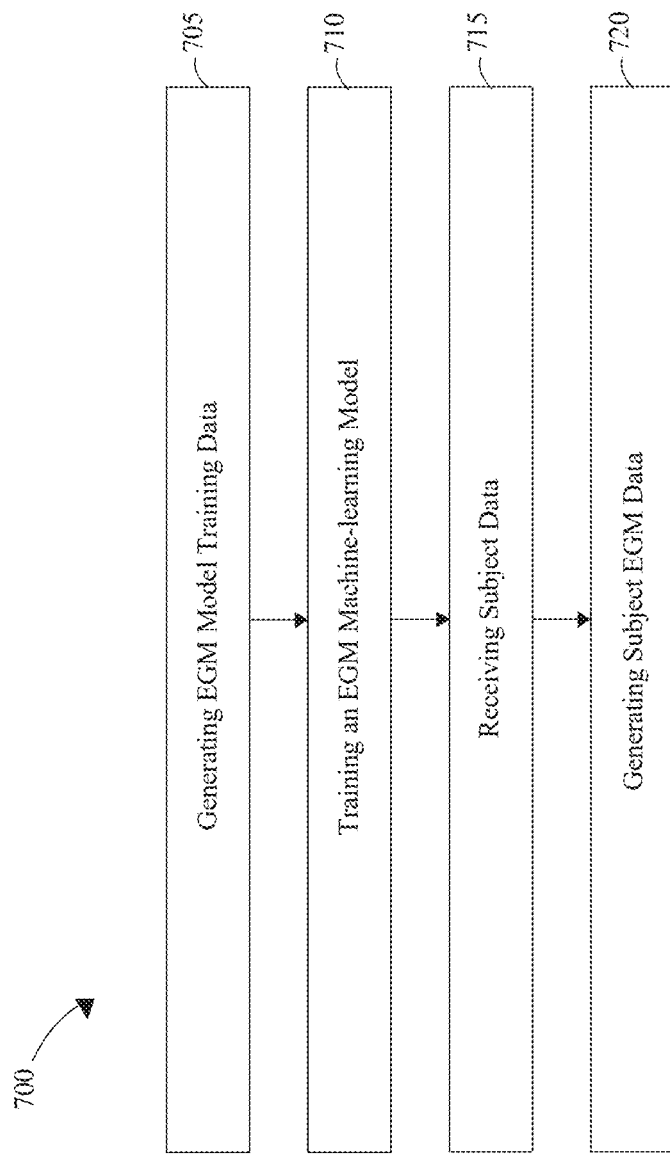
FIG. 7 illustrates a flow diagram of an exemplary method for generating pseudo-EGM data from ECG data.

Referring now to FIG. 7, a flow diagram of an exemplary method 700 for generating pseudo-EGM data from ECG data is illustrated. Method 700 contains a step 705 of generating, using at least a processor, EGM model training data, wherein generating the EGM model training data includes receiving the EGM model training data, wherein the EGM model training data includes exemplary ECG data correlated to exemplary EGM data and time synchronizing the exemplary ECG data and the exemplary EGM data. In some embodiments, generating the EGM model training data may include determining a first disturbance within the exemplary ECG data and the exemplary EGM data and aligning the exemplary ECG data and the exemplary EGM data as a function of the first disturbance. In some embodiments, generating the EGM model training data may include updating the EGM model training data as a function of an input and output of the trained EGM machine-learning model and iteratively training the EGM machine-learning model as a function of the updated EGM model training data. These may be implemented as reference to FIGS. 1-6.

With continued reference to FIG. 7, method 700 contains a step 710 of training, using at least a processor, an EGM machine-learning model using the EGM model training data. This may be implemented as reference to FIGS. 1-6.

With continued reference to FIG. 7, method 700 contains a step 715 of receiving, using at least a processor, subject data, wherein the subject data includes subject ECG data. In some embodiments, receiving the subject ECG data may include receiving the subject ECG data from at least an ECG sensor. In some embodiments, the at least an ECG sensor may include a 12 lead ECG. These may be implemented as reference to FIGS. 1-6.

With continued reference to FIG. 7, method 700 contains a step 720 of generating, using at least a processor, subject EGM data as a function of the subject ECG data using the trained EGM machine-learning model. In some embodiments, generating the subject EGM data as a function of the ECG data may include time synchronizing the subject ECG data with the EGM model training data, splitting the synchronized subject ECG data into a plurality of segments and generating the subject EGM data as a function of the plurality of segments of the synchronized subject ECG data. In some embodiments, the subject EGM data may include a continuous distribution of EGM data. In some embodiments, generating the subject EGM data as a function of the subject ECG data may include classifying the subject ECG data of the subject data into one or more subject cohorts and generating the subject EGM data as a function of the one or more subject cohorts. In some embodiments, method 700 may further include generating, using the at least a processor, a diagnostic output as a function of the subject EGM data. In some embodiments, method 700 may further include transmitting, using the at least a processor, the subject EGM data to a user device to display the subject EGM data to a user. These may be implemented as reference to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
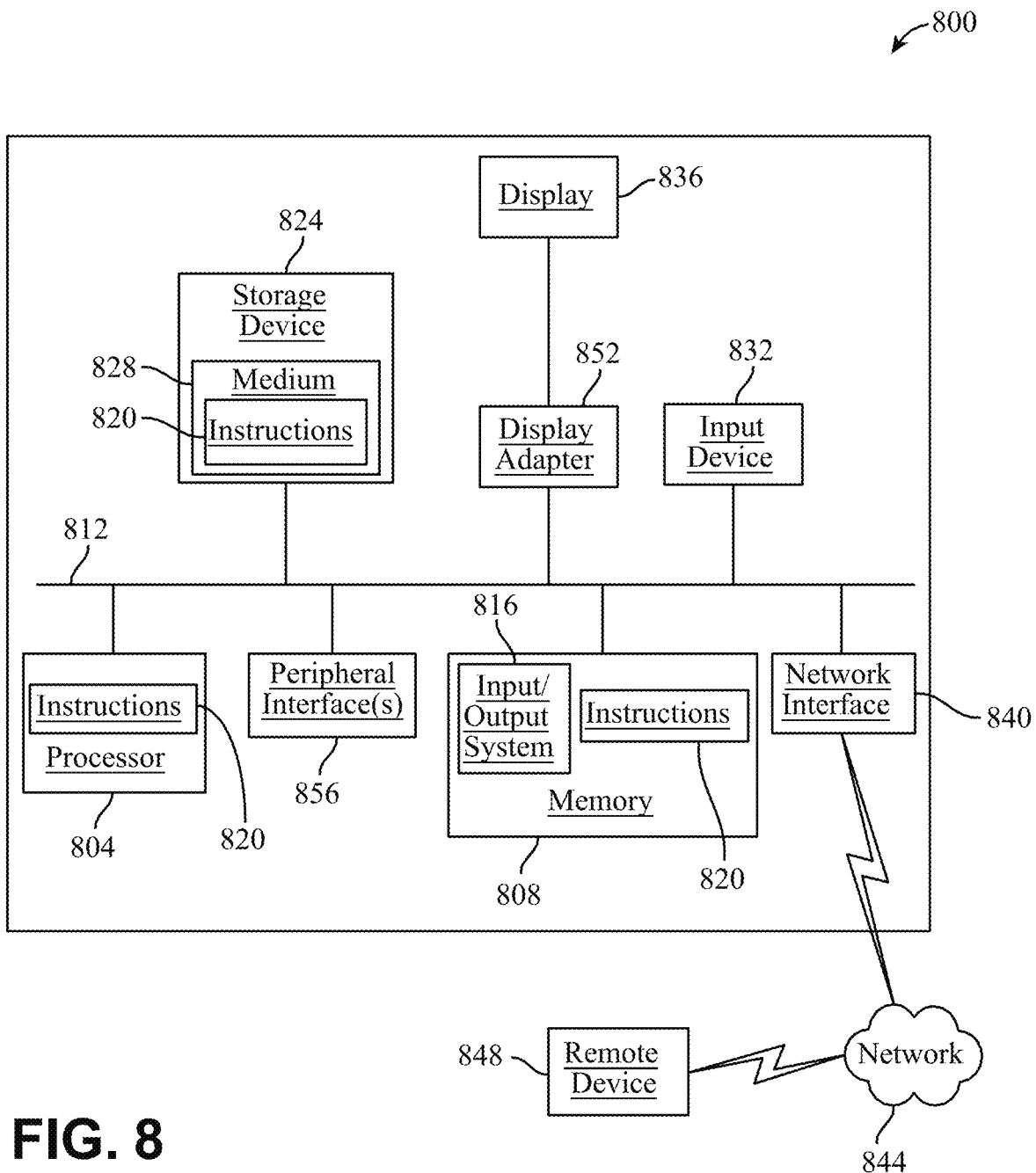
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and memory 808 that communicate with each other, and with other components, via a bus 812. Bus 812 may include any of several types of bus structures including, but not limited to, memory bus, memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIRE-WIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and apparatuses according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for generating pseudo-electrogram (EGM) data from electrocardiogram (ECG) data, the apparatus comprising:
   at least a processor; and
   a memory communicatively connected to the at least a processor, wherein the memory contains instructions configuring the at least a processor to:

generate EGM model training data, wherein generating the EGM model training data comprises:
    receiving the EGM model training data, wherein the EGM model training data comprises exemplary ECG data correlated to exemplary EGM data; and
    time synchronizing the exemplary ECG data and the exemplary EGM data using a synchronization machine learning model trained using synchronization training data configured to correlate time synchronized ECG data and time synchronized EGM data, wherein the synchronization training data is iteratively updated using a feedback loop;
train an EGM machine-learning model using the EGM model training data;
receive subject data, wherein the subject data comprises subject ECG data; and
generate subject EGM data as a function of the subject ECG data using the trained EGM machine-learning model.

2. The apparatus of claim 1, wherein generating the EGM model training data comprises:
    determining a first disturbance within the exemplary ECG data and the exemplary EGM data; and
    aligning the exemplary ECG data and the exemplary EGM data as a function of the first disturbance.

3. The apparatus of claim 1, wherein generating the EGM model training data comprises:
    updating the EGM model training data as a function of an input and output of the trained EGM machine-learning model; and
    iteratively training the EGM machine-learning model as a function of the updated EGM model training data.

4. The apparatus of claim 1, wherein receiving the subject ECG data comprises receiving the subject ECG data from at least an ECG sensor.

5. The apparatus of claim 4, wherein the at least an ECG sensor comprises a 12 lead ECG.

6. The apparatus of claim 1, wherein generating the subject EGM data as a function of the ECG data comprises:
    time synchronizing the subject ECG data with the EGM model training data;
    splitting the synchronized subject ECG data into a plurality of segments; and
    generating the subject EGM data as a function of the plurality of segments of the synchronized subject ECG data.

7. The apparatus of claim 1, wherein the subject EGM data comprises a continuous distribution of EGM data.

8. The apparatus of claim 1, wherein generating the subject EGM data as a function of the subject ECG data comprises:
    classifying the subject ECG data of the subject data into one or more subject cohorts; and
    generating the subject EGM data as a function of the one or more subject cohorts.

9. The apparatus of claim 1, wherein the memory contains instructions configuring the at least a processor to generate a diagnostic output as a function of the subject EGM data.

10. The apparatus of claim 1, wherein the memory contains instructions configuring the at least a processor to transmit the subject EGM data to a user device to display the subject EGM data to a user.

11. A method for generating pseudo-electrogram (EGM) data from electrocardiogram (ECG) data, the method comprising:
    generating, using at least a processor, EGM model training data, wherein generating the EGM model training data comprises:
        receiving the EGM model training data, wherein the EGM model training data comprises exemplary ECG data correlated to exemplary EGM data; and
        time synchronizing the exemplary ECG data and the exemplary EGM data using a synchronization machine learning model trained using synchronization training data configured to correlate time synchronized ECG data and time synchronized EGM data, wherein the synchronization training data is iteratively updated using a feedback loop;
    training, using the at least a processor, an EGM machine-learning model using the EGM model training data;
    receiving, using the at least a processor, subject data, wherein the subject data comprises subject ECG data; and
    generating, using the at least a processor, subject EGM data as a function of the subject ECG data using the trained EGM machine-learning model.

12. The method of claim 11, wherein generating the EGM model training data comprises:
    determining a first disturbance within the exemplary ECG data and the exemplary EGM data; and
    aligning the exemplary ECG data and the exemplary EGM data as a function of the first disturbance.

13. The method of claim 11, wherein generating the EGM model training data comprises:
    updating the EGM model training data as a function of an input and output of the trained EGM machine-learning model; and
    iteratively training the EGM machine-learning model as a function of the updated EGM model training data.

14. The method of claim 11, wherein receiving the subject ECG data comprises receiving the subject ECG data from at least an ECG sensor.

15. The method of claim 14, wherein the at least an ECG sensor comprises a 12 lead ECG.

16. The method of claim 11, wherein generating the subject EGM data as a function of the ECG data comprises:
    time synchronizing the subject ECG data with the EGM model training data;
    splitting the synchronized subject ECG data into a plurality of segments; and
    generating the subject EGM data as a function of the plurality of segments of the synchronized subject ECG data.

17. The method of claim 11, wherein the subject EGM data comprises a continuous distribution of EGM data.

18. The method of claim 11, wherein generating the subject EGM data as a function of the subject ECG data comprises:
    classifying the subject ECG data of the subject data into one or more subject cohorts; and
    generating the subject EGM data as a function of the one or more subject cohorts.

19. The method of claim 11, further comprising:
    generating, using the at least a processor, a diagnostic output as a function of the subject EGM data.

20. The method of claim 11, further comprising:
    transmitting, using the at least a processor, the subject EGM data to a user device to display the subject EGM data to a user.

* * * * *